(12) United States Patent
Blaschuk et al.

(10) Patent No.: US 6,303,576 B1
(45) Date of Patent: Oct. 16, 2001

(54) COMPOUNDS AND METHODS FOR MODULATING β-CATENIN MEDIATED GENE EXPRESSION

(75) Inventors: Orest W. Blaschuk, Westmount (CA); Stephen Byers, Washington, DC (US); Barbara J. Gour, Kemptville (CA)

(73) Assignee: Adherex Technologies Inc., Ottawa (CA)

( * ) Notice: Subject to any disclaimer, the term of this patent is extended or adjusted under 35 U.S.C. 154(b) by 0 days.

(21) Appl. No.: 09/296,089

(22) Filed: Apr. 21, 1999

(51) Int. Cl.$^7$ .................................................. A61K 38/00
(52) U.S. Cl. .................................. 514/14; 435/5; 435/6; 435/91.1; 435/91.2; 530/317
(58) Field of Search ................................ 530/317; 514/9; 435/6, 5, 91.1, 91.2

(56) References Cited

U.S. PATENT DOCUMENTS

| | | | |
|---|---|---|---|
| 5,652,122 | 7/1997 | Frankel et al. | 435/69.7 |
| 6,031,072 | * 2/2000 | Blaschuk et al. | 530/317 |

FOREIGN PATENT DOCUMENTS

| | | | |
|---|---|---|---|
| WO98/45319 | * 5/1998 | (CA) | G01N/33/68 |
| 199 09 251 A1 | 8/1999 | (DE) . | |
| WO98/49561 | * 5/1998 | (GB) | G01N/33/68 |
| WO 98/42296 | 10/1998 | (WO) . | |
| WO 98/45319 | 10/1998 | (WO) . | |
| WO 98/49561 | 11/1998 | (WO) . | |
| WO 99/42481 | 8/1999 | (WO) . | |

OTHER PUBLICATIONS

Aberle et al., "β–catenin is a target for the ubiquitin–proteasome pathway," *The EMBO Journal* 16(13): 3797–3804, 1997.

Easwaran et al., "The Ubiquitin/Proteosome Pathway And Apc Regulation Of β–Catenin/Lef Signaling," *Mol. Biol. Cell* 9:p. 248a, Abstract No. 1440, 1998.

Gat et al., "De Novo Hair Follicel Morphogenesis and Hair Tumors in Mice Expressing a Truncated β–Catenin in Skin," *Cell* 95: 605–614, 1998.

Oro and Scott, "Splitting Hairs: Dissecting Roles of Signaling Systems in Epidermal Development," *Cell* 95: 575–578, 1998.

Orford et al., "Serine Phosporylation–regulated Ubiquitination and Degradation of β–Catenin,"*The Journal of Biological Chemistry* 272(40): 24735–24738, 1997.

Salomon et al., "Regulation of β–Catenin Levels and Localization by Overexpression of Plakoglobin and Inhibition of the Ubiquitin–Proteasome System," *The Journal of Cell Biology* 139(5): 1325–1335, 1997.

Torchia et al., "The transcriptional co–activator p/CIP binds CBP and mediates nuclear–receptor function," *Nature* 387: 677–684, 1997.

Willert and Nusse, "β–catenin: a key mediator of Wnt signaling," *Current Opinion in Genetics and Development* 8: 95–102, 1998.

Zhang et al., "Destabilization of β–catenin by mutations in presenilin–1 potentiates neuronal apoptosis," *Nature* 395: 698–702, 1998.

DE 19909251 A1, Derwent English Abstract, Accession No. 1999–470389/199940, Aug. 1999.

He et al., "Identification of c–MYC as a Target of the APC Pathway," *Science* 281:1509–1512, Sep. 1998.

Heery et al., "A signature motif in transcriptional co–activators mediates binding to nuclear receptors," *Nature* 387 :733–736, Jun. 1997.

Hülsken et al., "E–Cadherin and APC Compete for the Interaction with β–Catenin and the Cytoskeleton," *J. Cell Biology* 127(6):2061–2069, Dec. 1994.

Hülsken et al., "E–Cadherin amd APC Compete for the Interaction with βCatenin and the Cytoskeleton," EMBL Sequence Database, Accession No. A38973, Jan. 1996.

Hülsken et al., "E–Cadherin and APC Compete for the Interation with β–Catenin and the Cytoskeleton," EMBL Sequence Database, Accession No. P35222, Feb. 1994.

McCrea et al., "Plakoglobin and β–Catenin: Distinct But Closely Related," *Science* 257:1142–1144, Aug. 1992.

Zhang et al., "Destabilization of β–Catenin by mutations in presenilin–1 potentiates neuronal apoptosis," *Nature* 395:698–702, Oct. 1998.

* cited by examiner

*Primary Examiner*—W. Gary Jones
*Assistant Examiner*—Janell E. Taylor
(74) *Attorney, Agent, or Firm*—Seed Intellectual Property Law Group PLLC (57) ABSTRACT

Modulating agents for inhibiting β-catenin mediated gene expression are provided. The modulating agents comprise one or more of: (1) the peptide sequence LXXLL (SEQ ID NO:1); or (2) a peptide analogue or peptidomimetic thereof. Methods for using such modulating agents for modulating β-catenin mediated gene expression and cellular differentiation in a variety of contexts (e.g., for modulating hair growth or treating cancer or Alzheimer's disease) are provided.

25 Claims, 1 Drawing Sheet

Fig. 1

SEQUENCE LISTING

<160> NUMBER OF SEQ ID NOS: 37

<210> SEQ ID NO 1
<211> LENGTH: 5
<212> TYPE: PRT
<213> ORGANISM: Homo sapien and Mus muculus
<220> FEATURE:
<221> NAME/KEY: VARIANT
<222> LOCATION: (1)...(5)
<223> OTHER INFORMATION: Xaa = Any Amino Acid

<400> SEQUENCE: 1

Leu Xaa Xaa Leu Leu
 1               5

<210> SEQ ID NO 2
<211> LENGTH: 5
<212> TYPE: PRT
<213> ORGANISM: Homo sapien

<400> SEQUENCE: 2

Leu Thr Lys Leu Leu
 1               5

<210> SEQ ID NO 3
<211> LENGTH: 5
<212> TYPE: PRT
<213> ORGANISM: Homo sapien

<400> SEQUENCE: 3

Leu His Asn Leu Leu
 1               5

<210> SEQ ID NO 4
<211> LENGTH: 5
<212> TYPE: PRT
<213> ORGANISM: Homo sapien

<400> SEQUENCE: 4

Leu Val Gln Leu Leu
 1               5

<210> SEQ ID NO 5
<211> LENGTH: 5
<212> TYPE: PRT
<213> ORGANISM: Homo sapien

<400> SEQUENCE: 5

Leu Thr Glu Leu Leu
 1               5

<210> SEQ ID NO 6
<211> LENGTH: 8
<212> TYPE: PRT
<213> ORGANISM: Artificial Sequence
<220> FEATURE:
<223> OTHER INFORMATION: Representative modulating agent capable of
      inhibiting beta-catenin mediated gene
      transcription
<220> FEATURE:
<221> NAME/KEY: VARIANT
<222> LOCATION: (1)...(1)
<223> OTHER INFORMATION: N-terminal amino acid may be modified by
      acetylation or alkoxybenzylation
<220> FEATURE:
<221> NAME/KEY: VARIANT

```
<222> LOCATION: (8)...(8)
<223> OTHER INFORMATION: C-terminal amino acid may be modified by an
      amide or ester

<400> SEQUENCE: 6

Ile Pro Glu Leu Thr Lys Leu Leu
 1               5

<210> SEQ ID NO 7
<211> LENGTH: 8
<212> TYPE: PRT
<213> ORGANISM: Artificial Sequence
<220> FEATURE:
<223> OTHER INFORMATION: Representative modulating agent capable of
      inhibiting beta-catenin mediated gene
      transcription
<220> FEATURE:
<221> NAME/KEY: VARIANT
<222> LOCATION: (1)...(1)
<223> OTHER INFORMATION: N-terminal amino acid may be modified by
      acetylation or alkoxybenzylation
<220> FEATURE:
<221> NAME/KEY: VARIANT
<222> LOCATION: (8)...(8)
<223> OTHER INFORMATION: C-terminal amino acid may be modified by an
      amide or ester

<400> SEQUENCE: 7

Pro Glu Leu Thr Lys Leu Leu Asn
 1               5

<210> SEQ ID NO 8
<211> LENGTH: 8
<212> TYPE: PRT
<213> ORGANISM: Artificial Sequence
<220> FEATURE:
<223> OTHER INFORMATION: Representative modulating agent capable of
      inhibiting beta-catenin mediated gene
      transcription
<220> FEATURE:
<221> NAME/KEY: VARIANT
<222> LOCATION: (1)...(1)
<223> OTHER INFORMATION: N-terminal amino acid may be modified by
      acetylation or alkoxybenzylation
<220> FEATURE:
<221> NAME/KEY: VARIANT
<222> LOCATION: (8)...(8)
<223> OTHER INFORMATION: C-terminal amino acid may be modified by an
      amide or ester

<400> SEQUENCE: 8

Glu Leu Thr Lys Leu Leu Asn Asp
 1               5

<210> SEQ ID NO 9
<211> LENGTH: 8
<212> TYPE: PRT
<213> ORGANISM: Artificial Sequence
<220> FEATURE:
<223> OTHER INFORMATION: Representative modulating agent capable of
      inhibiting beta-catenin mediated gene
      transcription
<220> FEATURE:
<221> NAME/KEY: VARIANT
<222> LOCATION: (1)...(1)
<223> OTHER INFORMATION: N-terminal amino acid may be modified by
      acetylation or alkoxybenzylation
<220> FEATURE:
<221> NAME/KEY: VARIANT
<222> LOCATION: (8)...(8)
<223> OTHER INFORMATION: C-terminal amino acid may be modified by an
      amide or ester
```

```
<400> SEQUENCE: 9

Leu Thr Lys Leu Leu Asn Asp Glu
 1               5

<210> SEQ ID NO 10
<211> LENGTH: 8
<212> TYPE: PRT
<213> ORGANISM: Artificial Sequence
<220> FEATURE:
<223> OTHER INFORMATION: Representative modulating agent capable of
      inhibiting beta-catenin mediated gene
      transcription
<220> FEATURE:
<221> NAME/KEY: VARIANT
<222> LOCATION: (1)...(1)
<223> OTHER INFORMATION: N-terminal amino acid may be modified by
      acetylation or alkoxybenzylation
<220> FEATURE:
<221> NAME/KEY: VARIANT
<222> LOCATION: (8)...(8)
<223> OTHER INFORMATION: C-terminal amino acid may be modified by an
      amide or ester

<400> SEQUENCE: 10

Ile Thr Thr Leu His Asn Leu Leu
 1               5

<210> SEQ ID NO 11
<211> LENGTH: 8
<212> TYPE: PRT
<213> ORGANISM: Artificial Sequence
<220> FEATURE:
<223> OTHER INFORMATION: Representative modulating agent capable of
      inhibiting beta-catenin mediated gene
      transcription
<220> FEATURE:
<221> NAME/KEY: VARIANT
<222> LOCATION: (1)...(1)
<223> OTHER INFORMATION: N-terminal amino acid may be modified by
      acetylation or alkoxybenzylation
<220> FEATURE:
<221> NAME/KEY: VARIANT
<222> LOCATION: (8)...(8)
<223> OTHER INFORMATION: C-terminal amino acid may be modified by an
      amide or ester

<400> SEQUENCE: 11

Thr Thr Leu His Asn Leu Leu Leu
 1               5

<210> SEQ ID NO 12
<211> LENGTH: 8
<212> TYPE: PRT
<213> ORGANISM: Artificial Sequence
<220> FEATURE:
<223> OTHER INFORMATION: Representative modulating agent capable of
      inhibiting beta-catenin mediated gene
      transcription
<220> FEATURE:
<221> NAME/KEY: VARIANT
<222> LOCATION: (1)...(1)
<223> OTHER INFORMATION: N-terminal amino acid may be modified by
      acetylation or alkoxybenzylation
<220> FEATURE:
<221> NAME/KEY: VARIANT
<222> LOCATION: (8)...(8)
<223> OTHER INFORMATION: C-terminal amino acid may be modified by an
      amide or ester

<400> SEQUENCE: 12

Thr Leu His Asn Leu Leu Leu His
 1               5
```

```
<210> SEQ ID NO 13
<211> LENGTH: 8
<212> TYPE: PRT
<213> ORGANISM: Artificial Sequence
<220> FEATURE:
<223> OTHER INFORMATION: Representative modulating agent capable of
      inhibiting beta-catenin mediated gene
      transcription
<220> FEATURE:
<221> NAME/KEY: VARIANT
<222> LOCATION: (1)...(1)
<223> OTHER INFORMATION: N-terminal amino acid may be modified by
      acetylation or alkoxybenzylation
<220> FEATURE:
<221> NAME/KEY: VARIANT
<222> LOCATION: (8)...(8)
<223> OTHER INFORMATION: C-terminal amino acid may be modified by an
      amide or ester

<400> SEQUENCE: 13

Leu His Asn Leu Leu Leu His Gln
 1               5

<210> SEQ ID NO 14
<211> LENGTH: 8
<212> TYPE: PRT
<213> ORGANISM: Artificial Sequence
<220> FEATURE:
<223> OTHER INFORMATION: Representative modulating agent capable of
      inhibiting beta-catenin mediated gene
      transcription
<220> FEATURE:
<221> NAME/KEY: VARIANT
<222> LOCATION: (1)...(1)
<223> OTHER INFORMATION: N-terminal amino acid may be modified by
      acetylation or alkoxybenzylation
<220> FEATURE:
<221> NAME/KEY: VARIANT
<222> LOCATION: (8)...(8)
<223> OTHER INFORMATION: C-terminal amino acid may be modified by an
      amide or ester

<400> SEQUENCE: 14

Leu Gly Thr Leu Val Gln Leu Leu
 1               5

<210> SEQ ID NO 15
<211> LENGTH: 8
<212> TYPE: PRT
<213> ORGANISM: Artificial Sequence
<220> FEATURE:
<223> OTHER INFORMATION: Representative modulating agent capable of
      inhibiting beta-catenin mediated gene
      transcription
<220> FEATURE:
<221> NAME/KEY: VARIANT
<222> LOCATION: (1)...(1)
<223> OTHER INFORMATION: N-terminal amino acid may be modified by
      acetylation or alkoxybenzylation
<220> FEATURE:
<221> NAME/KEY: VARIANT
<222> LOCATION: (8)...(8)
<223> OTHER INFORMATION: C-terminal amino acid may be modified by an
      amide or ester

<400> SEQUENCE: 15

Gly Thr Leu Val Gln Leu Leu Gly
 1               5

<210> SEQ ID NO 16
<211> LENGTH: 8
```

```
<212> TYPE: PRT
<213> ORGANISM: Artificial Sequence
<220> FEATURE:
<223> OTHER INFORMATION: Representative modulating agent capable of
      inhibiting beta-catenin mediated gene
      transcription
<220> FEATURE:
<221> NAME/KEY: VARIANT
<222> LOCATION: (1)...(1)
<223> OTHER INFORMATION: N-terminal amino acid may be modified by
      acetylation or alkoxybenzylation
<220> FEATURE:
<221> NAME/KEY: VARIANT
<222> LOCATION: (8)...(8)
<223> OTHER INFORMATION: C-terminal amino acid may be modified by an
      amide or ester

<400> SEQUENCE: 16

Thr Leu Val Gln Leu Leu Gly Ser
 1               5

<210> SEQ ID NO 17
<211> LENGTH: 8
<212> TYPE: PRT
<213> ORGANISM: Artificial Sequence
<220> FEATURE:
<223> OTHER INFORMATION: Representative modulating agent capable of
      inhibiting beta-catenin mediated gene
      transcription
<220> FEATURE:
<221> NAME/KEY: VARIANT
<222> LOCATION: (1)...(1)
<223> OTHER INFORMATION: N-terminal amino acid may be modified by
      acetylation or alkoxybenzylation
<220> FEATURE:
<221> NAME/KEY: VARIANT
<222> LOCATION: (8)...(8)
<223> OTHER INFORMATION: C-terminal amino acid may be modified by an
      amide or ester

<400> SEQUENCE: 17

Leu Val Gln Leu Leu Gly Ser Asp
 1               5

<210> SEQ ID NO 18
<211> LENGTH: 8
<212> TYPE: PRT
<213> ORGANISM: Artificial Sequence
<220> FEATURE:
<223> OTHER INFORMATION: Representative modulating agent capable of
      inhibiting beta-catenin mediated gene
      transcription
<220> FEATURE:
<221> NAME/KEY: VARIANT
<222> LOCATION: (1)...(1)
<223> OTHER INFORMATION: N-terminal amino acid may be modified by
      acetylation or alkoxybenzylation
<220> FEATURE:
<221> NAME/KEY: VARIANT
<222> LOCATION: (8)...(8)
<223> OTHER INFORMATION: C-terminal amino acid may be modified by an
      amide or ester

<400> SEQUENCE: 18

Ile Pro Arg Leu Val Gln Leu Leu
 1               5

<210> SEQ ID NO 19
<211> LENGTH: 8
<212> TYPE: PRT
<213> ORGANISM: Artificial Sequence
<220> FEATURE:
<223> OTHER INFORMATION: Representative modulating agent capable of
```

```
      inhibiting beta-catenin mediated gene
      transcription
<220> FEATURE:
<221> NAME/KEY: VARIANT
<222> LOCATION: (1)...(1)
<223> OTHER INFORMATION: N-terminal amino acid may be modified by
      acetylation or alkoxybenzylation
<220> FEATURE:
<221> NAME/KEY: VARIANT
<222> LOCATION: (8)...(8)
<223> OTHER INFORMATION: C-terminal amino acid may be modified by an
      amide or ester

<400> SEQUENCE: 19

Pro Arg Leu Val Gln Leu Leu Val
 1               5

<210> SEQ ID NO 20
<211> LENGTH: 8
<212> TYPE: PRT
<213> ORGANISM: Artificial Sequence
<220> FEATURE:
<223> OTHER INFORMATION: Representative modulating agent capable of
      inhibiting beta-catenin mediated gene
      transcription
<220> FEATURE:
<221> NAME/KEY: VARIANT
<222> LOCATION: (1)...(1)
<223> OTHER INFORMATION: N-terminal amino acid may be modified by
      acetylation or alkoxybenzylation
<220> FEATURE:
<221> NAME/KEY: VARIANT
<222> LOCATION: (8)...(8)
<223> OTHER INFORMATION: C-terminal amino acid may be modified by an
      amide or ester

<400> SEQUENCE: 20

Arg Leu Val Gln Leu Leu Val Arg
 1               5

<210> SEQ ID NO 21
<211> LENGTH: 8
<212> TYPE: PRT
<213> ORGANISM: Artificial Sequence
<220> FEATURE:
<223> OTHER INFORMATION: Representative modulating agent capable of
      inhibiting beta-catenin mediated gene
      transcription
<220> FEATURE:
<221> NAME/KEY: VARIANT
<222> LOCATION: (1)...(1)
<223> OTHER INFORMATION: N-terminal amino acid may be modified by
      acetylation or alkoxybenzylation
<220> FEATURE:
<221> NAME/KEY: VARIANT
<222> LOCATION: (8)...(8)
<223> OTHER INFORMATION: C-terminal amino acid may be modified by an
      amide or ester

<400> SEQUENCE: 21

Leu Val Gln Leu Leu Val Arg Ala
 1               5

<210> SEQ ID NO 22
<211> LENGTH: 8
<212> TYPE: PRT
<213> ORGANISM: Artificial Sequence
<220> FEATURE:
<223> OTHER INFORMATION: Representative modulating agent capable of
      inhibiting beta-catenin mediated gene
      transcription
<220> FEATURE:
<221> NAME/KEY: VARIANT
```

```
<222> LOCATION: (1)...(1)
<223> OTHER INFORMATION: N-terminal amino acid may be modified by
      acetylation or alkoxybenzylation
<220> FEATURE:
<221> NAME/KEY: VARIANT
<222> LOCATION: (8)...(8)
<223> OTHER INFORMATION: C-terminal amino acid may be modified by an
      amide or ester

<400> SEQUENCE: 22

Thr Ala Pro Leu Thr Glu Leu Leu
 1               5

<210> SEQ ID NO 23
<211> LENGTH: 8
<212> TYPE: PRT
<213> ORGANISM: Artificial Sequence
<220> FEATURE:
<223> OTHER INFORMATION: Representative modulating agent capable of
      inhibiting beta-catenin mediated gene
      transcription
<220> FEATURE:
<221> NAME/KEY: VARIANT
<222> LOCATION: (1)...(1)
<223> OTHER INFORMATION: N-terminal amino acid may be modified by
      acetylation or alkoxybenzylation
<220> FEATURE:
<221> NAME/KEY: VARIANT
<222> LOCATION: (8)...(8)
<223> OTHER INFORMATION: C-terminal amino acid may be modified by an
      amide or ester

<400> SEQUENCE: 23

Ala Pro Leu Thr Glu Leu Leu His
 1               5

<210> SEQ ID NO 24
<211> LENGTH: 8
<212> TYPE: PRT
<213> ORGANISM: Artificial Sequence
<220> FEATURE:
<223> OTHER INFORMATION: Representative modulating agent capable of
      inhibiting beta-catenin mediated gene
      transcription
<220> FEATURE:
<221> NAME/KEY: VARIANT
<222> LOCATION: (1)...(1)
<223> OTHER INFORMATION: N-terminal amino acid may be modified by
      acetylation or alkoxybenzylation
<220> FEATURE:
<221> NAME/KEY: VARIANT
<222> LOCATION: (8)...(8)
<223> OTHER INFORMATION: C-terminal amino acid may be modified by an
      amide or ester

<400> SEQUENCE: 24

Pro Leu Thr Glu Leu Leu His Ser
 1               5

<210> SEQ ID NO 25
<211> LENGTH: 8
<212> TYPE: PRT
<213> ORGANISM: Artificial Sequence
<220> FEATURE:
<223> OTHER INFORMATION: Representative modulating agent capable of
      inhibiting beta-catenin mediated gene
      transcription
<220> FEATURE:
<221> NAME/KEY: VARIANT
<222> LOCATION: (1)...(1)
<223> OTHER INFORMATION: N-terminal amino acid may be modified by
      acetylation or alkoxybenzylation
<220> FEATURE:
```

```
<221> NAME/KEY: VARIANT
<222> LOCATION: (8)...(8)
<223> OTHER INFORMATION: C-terminal amino acid may be modified by an
      amide or ester

<400> SEQUENCE: 25

Leu Thr Glu Leu Leu His Ser Arg
 1               5

<210> SEQ ID NO 26
<211> LENGTH: 11
<212> TYPE: PRT
<213> ORGANISM: Homo sapien

<400> SEQUENCE: 26

Ile Pro Glu Leu Thr Lys Leu Leu Asn Asp Glu
 1               5                  10

<210> SEQ ID NO 27
<211> LENGTH: 11
<212> TYPE: PRT
<213> ORGANISM: Homo sapien

<400> SEQUENCE: 27

Ile Thr Thr Leu His Asn Leu Leu Leu His Gln
 1               5                  10

<210> SEQ ID NO 28
<211> LENGTH: 11
<212> TYPE: PRT
<213> ORGANISM: Homo sapien

<400> SEQUENCE: 28

Leu Gly Thr Leu Val Gln Leu Leu Gly Ser Asp
 1               5                  10

<210> SEQ ID NO 29
<211> LENGTH: 11
<212> TYPE: PRT
<213> ORGANISM: Homo sapien

<400> SEQUENCE: 29

Ile Pro Arg Leu Val Gln Leu Leu Val Arg Ala
 1               5                  10

<210> SEQ ID NO 30
<211> LENGTH: 11
<212> TYPE: PRT
<213> ORGANISM: Homo sapien

<400> SEQUENCE: 30

Thr Ala Pro Leu Thr Glu Leu Leu His Ser Arg
 1               5                  10

<210> SEQ ID NO 31
<211> LENGTH: 7
<212> TYPE: PRT
<213> ORGANISM: Artificial Sequence
<220> FEATURE:
<223> OTHER INFORMATION: Representative cyclic modulating agent capable
      of inhibiting beta-catenin mediated gene transcription
<220> FEATURE:
<221> NAME/KEY: VARIANT
<222> LOCATION: (1)...(7)
<223> OTHER INFORMATION: Xaa = Any Amino Acid

<400> SEQUENCE: 31
```

```
Cys Leu Xaa Xaa Leu Leu Cys
  1               5
```

<210> SEQ ID NO 32
<211> LENGTH: 4
<212> TYPE: PRT
<213> ORGANISM: Artificial Sequence
<220> FEATURE:
<223> OTHER INFORMATION: Peptide to demonstrate cyclization method

<400> SEQUENCE: 32

```
Trp Gly Gly Trp
  1
```

<210> SEQ ID NO 33
<211> LENGTH: 16
<212> TYPE: PRT
<213> ORGANISM: Drosophila melanogaster

<400> SEQUENCE: 33

```
Arg Gln Ile Lys Ile Trp Phe Gln Asn Arg Arg Met Lys Trp Lys Lys
  1               5                  10                  15
```

<210> SEQ ID NO 34
<211> LENGTH: 16
<212> TYPE: PRT
<213> ORGANISM: Drosophila melanogaster

<400> SEQUENCE: 34

```
Arg Gln Ile Lys Ile Trp Pro Gln Asn Arg Arg Asn Lys Trp Lys Lys
  1               5                  10                  15
```

<210> SEQ ID NO 35
<211> LENGTH: 16
<212> TYPE: PRT
<213> ORGANISM: Artificial Sequence
<220> FEATURE:
<223> OTHER INFORMATION: Analogue of Drosphilia Antennapedia protein

<400> SEQUENCE: 35

```
Lys Lys Trp Lys Lys Trp Trp Lys Lys Trp Trp Lys Lys Trp Lys Lys
  1               5                  10                  15
```

<210> SEQ ID NO 36
<211> LENGTH: 18
<212> TYPE: PRT
<213> ORGANISM: Artificial Sequence
<220> FEATURE:
<223> OTHER INFORMATION: Alpha-helix amphipathic model peptide

<400> SEQUENCE: 36

```
Lys Leu Ala Leu Lys Leu Ala Leu Lys Leu Ala Lys Ala Ala Leu Lys
  1               5                  10                  15

Leu Ala
```

<210> SEQ ID NO 37
<211> LENGTH: 11
<212> TYPE: PRT
<213> ORGANISM: Human immunodeficiency virus

<400> SEQUENCE: 37

```
Tyr Gly Arg Lys Lys Arg Arg Gln Arg Arg Arg
  1               5                  10
```

COMPOUNDS AND METHODS FOR MODULATING β-CATENIN MEDIATED GENE EXPRESSION

TECHNICAL FIELD

The present invention relates generally to compounds and methods for use in modulating β-catenin mediated gene expression and cellular differentiation. The invention is more specifically related to modulating agents capable of affecting the interaction between β-catenin and transcription factors, and to therapeutic methods employing such agents.

BACKGROUND OF THE INVENTION

β-catenin is a cytoplasmic protein that is critical for classical cadherin-mediated intercellular adhesion. Inside the cell, a β-catenin/α-catenin complex interacts with the second cytoplasmic domain (CP2) of the classical cadherins. In the absence of this β-catenin/α-catenin complex, the classical cadherins cannot promote cell adhesion (see Wheelock et al., Current Topics in Membranes 43:169–185, 1996).

In addition to its role in cell adhesion, β-catenin is also a key component of certain cellular signaling pathways, leading to activation of gene expression and a variety of developmental and disease processes, such as differentiation, cancer and Alzheimer's disease. In particular, β-catenin functions in Wnt-mediated signaling, associating with LEF-1/TCF DNA binding proteins to form a transcription factor (see Willert and Nusse, Genetics and Development 8:95–102, 1998). β-catenin-mediated signaling is involved in a variety of developmental processes, including cellular differentiation. For example, skin cells expressing a stabilized form of β-catenin display increased hair growth (Gat et al., Cell 95:605–614, 1998; Ono et al., Cell 95:575–578, 1998). Thus, therapies based on modulating β-catenin mediated gene expression have potential for altering cell differentiation and, in certain instances, hair growth. Such therapies could further be used in the treatment of cancer and Alzheimer's disease. However, there are presently no available therapies for inhibiting β-catenin-mediated signaling.

Accordingly, there is a need in the art for improved methods for modulating β-catenin-mediated signal transduction and cellular differentiation. The present invention fulfills this need and further provides other related advantages.

SUMMARY OF THE INVENTION

The present invention provides methods for inhibiting β-catenin mediated gene transcription and cellular differentiation. Within certain aspects, the present invention provides modulating agents comprising one or more of: (a) the amino acid sequence LXXLL (SEQ ID NO:1); or (b) a peptide analogue or peptidomimetic of the amino acid sequence LXXLL (SEQ ID NO:1). Within certain embodiments, the modulating agent comprises the sequence LXXLL (SEQ ID NO:1) within a linear peptide or a cyclic peptide ring. Such modulating agents may, within certain embodiments, comprise a linear or cyclic peptide ranging from 3 to 16 amino acid residues in length. A modulating agent may further comprise an internalization moiety, such as an internalization sequence covalently linked to the modulating agent, a liposome that encapsulates the modulating agent or an antibody or ligand that binds to a cell surface receptor. Within further embodiments, any of the above modulating agents may be linked to a targeting agent and/or a drug.

Within other aspects, the present invention provides pharmaceutical compositions comprising a modulating agent as described above, in combination with a pharmaceutically acceptable carrier.

Within further related aspects, the present invention provides methods for modulating the activation of β-catenin mediated gene transcription in a cell, comprising contacting a cell with a modulating agent as described above.

Within further related aspects, the present invention provides methods for modulating differentiation of a cell, comprising contacting a cell with a modulating agent as described above.

In other aspects, methods are provided for modulating hair growth on a mammal, comprising administering to a mammal a modulating agent as described above. Such administration may be topical.

The present invention further provides, within other aspects, methods for treating cancer and/or inhibiting metastasis in a patient, comprising administering to a patient a modulating agent as described above.

Within further aspects, the present invention provides methods for inhibiting the development of Alzheimer's disease in a patient, comprising administering to a patient a modulating agent as described above.

The present invention further provides methods for modulating the activity of a retinoic acid receptor and/or androgen receptor in a cell, comprising contacting a cell with a modulating agent as described above.

These and other aspects of the invention will become evident upon reference to the following detailed description and attached drawings. All references disclosed herein are hereby incorporated by reference in their entirety as if each were individually noted for incorporation.

DETAILED DESCRIPTION OF THE INVENTION

As noted above, the present invention provides methods for modulating β-catenin mediated gene transcription and cellular differentiation. The present invention is based, in part, upon the discovery that β-catenin contains LXXLL (SEQ ID NO:1) repeats, which are involved in protein interactions necessary for β-catenin mediated transcriptional activation. In particular, β-catenin interacts with and regulates the activity of nuclear transcription factors such as retinoic acid and androgen receptors. Modulating agents that comprise a LXXLL (SEQ ID NO:1) sequence as described herein may be used to modulate β-catenin mediated gene transcription within a variety of contexts. For example, certain such agents may be used to inhibit hair growth or cellular differentiation. Other agents may inhibit cancer cell growth and metastasis, and/or the development of Alzheimer's disease. Agents may also be used to modulate the activity of retinoic acid and androgen receptors.

MODULATING AGENTS

As noted above, the term "modulating agent," as used herein, refers to a molecule comprising one or more of (1) an LXXLL (SEQ ID NO:1) motif; or (2) a peptide analogue or peptidomimetic thereof. A modulating agent is further capable of inhibiting β-catenin mediated gene transcription, as described herein. Within preferred embodiments, a modulating agent further comprises an internalization moiety, which is associated (covalently or noncovalently) with one or more of the above components.

The sequence LXXLL (SEQ ID NO:1) is a five-amino acid sequence in which L represents a leucine residue and each X is a residue of an independently selected amino acid. Both X residues may be the same amino acid, or may be different. Preferred LXXLL sequences include sequences that are present within a naturally-occurring β-catenin, such as a human β-catenin. Certain LXXLL (SEQ ID NO:1) sequences include LTKLL (SEQ ID NO:2), LHNLL (SEQ ID NO:3), LVQLL (SEQ ID NO:4) and LTELL (SEQ ID NO:5).

Peptide agents as described herein may, but need not, contain additional amino acid residues from β-catenin. Such additional residues may flank the LXXLL (SEQ ID NO:1) sequence in a native β-catenin molecule (i.e., may be adjacent to that sequence in a native β-catenin molecule). LXXLL (SEQ ID NO:1) and flanking sequences for β-catenin of a variety of organisms are known, and certain such sequences are shown in Table I. Flanking residue(s) may be present on the N-terminal and/or C-terminal side of the above peptide sequence, preferably on both sides. Preferably, at least three flanking amino acid residues are present in a peptide agent, as in the peptide sequences: IPELTKLL (SEQ ID NO:6), PELTKLLN (SEQ ID NO:7), ELTKLLND (SEQ ID NO:8), LTKLLNDE (SEQ ID NO:9), ITTLHNLL (SEQ ID NO:10), TTLHNLLL (SEQ ID NO:11), TLHNLLLH (SEQ ID NO:12), LHNLLLHQ (SEQ ID NO:13), LGTLVQLL (SEQ ID NO:14), GTLVQLLG (SEQ ID NO:15), TLVQLLGS (SEQ ID NO:16), LVQLLGSD (SEQ ID NO:17), IPRLVQLL (SEQ ID NO:18), PRLVQLLV (SEQ ID NO:19), RLVQLLVR (SEQ ID NO:20), LVQLLVRA (SEQ ID NO:21), TAPLTELL (SEQ ID NO:22), APLTELLH (SEQ ID NO:23), PLTELLHS (SEQ ID NO:24) and LTELLHSR (SEQ ID NO:25).

TABLE I

LXXLL Sequences for Human β-Catenin

| Amino Acids | Sequence |
|---|---|
| 153–163 | IPELTKLLNDE (SEQ ID NO:26) |
| 256–266 | ITTLHNLLLHQ (SEQ ID NO:27) |
| 402–412 | LGTLVQLLGSD (SEQ ID NO:28) |
| 533–543 | IPRLVQLLVRA (SEQ ID NO:29) |
| 637–647 | TAPLTELLHSR (SEQ ID NO:30) |

A modulating agent may consist entirely of a β-catenin sequence, or may additionally comprise further peptide and/or non-peptide regions, such as regions that facilitate cyclization, purification or other manipulation, and/or residues having a targeting or other function. Agents comprising derivatives of LXXLL (SEQ ID NO:1) having one or more side chain modifications are also contemplated. Modulating agents may further be associated (covalently or noncovalently) with a targeting agent, drug, solid support and/or detectable marker.

Certain preferred modulating agents comprise a peptide in which at least one terminal amino acid residue is modified (e.g., the N-terminal amino group is modified by, for example, acetylation or alkoxybenzylation and/or an amide or ester is formed at the C-terminus). The addition of at least one such group to a linear or cyclic peptide modulating agent may improve the activity of the agent. Certain preferred modulating agents contain modifications at the N— and C-terminal residues, such as peptides that contain an N-acetyl group and a C-terminal amide group.

Modulating agents, or peptide portions thereof, may be linear or cyclic peptides. A "linear" peptide is a peptide or salt thereof that does not contain an intramolecular covalent bond between two non-adjacent residues. Within preferred embodiments, linear peptide modulating agents typically comprise from 10 to about 20 amino acid residues derived from β-catenin, preferably from 10 to 16 amino acid residues derived from β-catenin.

The term "cyclic peptide," as used herein, refers to a peptide or salt thereof that comprises an intramolecular covalent bond between two non-adjacent residues, forming a cyclic peptide ring that comprises the LXXLL (SEQ ID NO:1) sequence. The intramolecular bond may be a backbone to backbone, side-chain to backbone or side-chain to side-chain bond (i.e., terminal functional groups of a linear peptide and/or side chain functional groups of a terminal or interior residue may be linked to achieve cyclization). Preferred intramolecular bonds include, but are not limited to, disulfide bonds; amide bonds between terminal functional groups, between residue side chains or between one terminal functional groups and one residue side chain; thioether bonds and $\delta_1,\delta_1$-ditryptophan or a derivative thereof. For example, a cyclic peptide may satisfy the formula C̲LXXLLC̲ (SEQ ID NO:31) in which the underline indicates cyclization, or may contain additional sequences that flank the LXXLL (SEQ ID NO:1) sequence within the peptide ring. Preferred cyclic peptide modulating agents generally comprise at least eight residues, and more preferably between 10 and 15 residues, within the cyclic peptide ring.

As noted above, modulating agents may be polypeptides or salts thereof, containing only amino acid residues linked by peptide bonds, or may additionally contain non-peptide regions, such as linkers. Peptide regions of a modulating agent may comprise residues of L-amino acids, D-amino acids, or any combination thereof. Amino acids may be from natural or non-natural sources, provided that at least one amino group and at least one carboxyl group are present in the molecule; α- and β-amino acids are generally preferred. The 20 L-amino acids commonly found in proteins are identified herein by the conventional three-letter or one-letter abbreviations.

A modulating agent may also contain rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation) and the like). Preferred derivatives include amino acids having a C-terminal amide group. Residues other than common amino acids that may be present with a modulating agent include, but are not limited to, 2-mercaptoaniline, 2-mercaptoproline, ornithine, diaminobutyric acid, α-aminoadipic acid, m-aminomethylbenzoic acid and α,β-diaminopropionic acid.

As noted above, a modulating agent may comprise a peptide analogue or a non-peptide peptidomimetic of a LXXLL (SEQ ID NO:1) sequence, provided that the analogue or peptidomimetic retains the ability to inhibit a β-catenin mediated response. In general, a peptide analogue may contain conservative substitutions such that the ability to modulate a β-catenin mediated response is not substantially diminished. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his. The critical determining feature of a peptide analogue is the ability to modulate a β-catenin mediated response. Such an ability may be evaluated using the representative assays provided herein.

A peptidomimetic is a non-peptide compound that is structurally similar to the peptide sequence LXXLL (SEQ ID NO:1), such that the peptidomimetic retains the ability to modulate a β-catenin mediated response, as described below. Peptidomimetics are organic compounds that mimic the three-dimensional shape of the peptide sequence LXXLL (SEQ ID NO:1). Peptidomimetics may be designed based on techniques that evaluate the three dimensional shape, such as nuclear magnetic resonance (NMR) and computational techniques. NMR is widely used for structural analysis of molecules. Cross-peak intensities in nuclear Overhauser enhancement (NOE) spectra, coupling constants and chemical shifts depend on the conformation of a compound. NOE data provide the interproton distance between protons through space. This information may be used to facilitate calculation of the lowest energy conformation for the peptide sequence LXXLL (SEQ ID NO:1). Once the lowest energy conformation is known, the three-dimensional shape to be mimicked is known. It should be understood that, within embodiments described herein, an analogue or peptidomimetic may be substituted for the sequence LXXLL (SEQ ID NO:1).

Peptide modulating agents (and peptide portions of modulating agents) as described herein may be synthesized by methods well known in the art, including chemical synthesis and recombinant DNA methods. For modulating agents up to about 50 residues in length, chemical synthesis may be performed using solution phase or solid phase peptide synthesis techniques, in which a peptide linkage occurs through the direct condensation of the α-amino group of one amino acid with the α-carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (see Gross and Meienhofer, eds., "The Peptides: Analysis, Synthesis, Biology," Vol. 1–4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful segment selection is necessary to minimize racemization during segment condensation. Solubility considerations are also a factor.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., *J. Am. Chem. Soc.* 85:2149, 1963, which involves assembling a linear peptide chain on a resin support using protected amino acids. Solid phase peptide synthesis typically utilizes either the Boc or Fmoc strategy. The Boc strategy uses a 1% cross-linked polystyrene resin. The standard protecting group for α-amino functions is the tert-butyloxycarbonyl (Boc) group. This group can be removed with dilute solutions of strong acids such as 25% trifluoroacetic acid (TFA). The next Boc-amino acid is typically coupled to the amino acyl resin using dicyclohexylcarbodiimide (DCC). Following completion of the assembly, the peptide-resin is treated with anhydrous HF to cleave the benzyl ester link and liberate the free peptide. Side-chain functional groups are usually blocked during synthesis by benzyl-derived blocking groups, which are also cleaved by HF. The free peptide is then extracted from the resin with a suitable solvent, purified and characterized. Newly synthesized peptides can be purified, for example, by gel filtration, HPLC, partition chromatography and/or ion-exchange chromatography, and may be characterized by, for example, mass spectrometry or amino acid sequence analysis. In the Boc strategy, C-terminal amidated peptides can be obtained using benzhydrylamine or methylbenzhydrylamine resins, which yield peptide amides directly upon cleavage with HF.

In the procedures discussed above, the selectivity of the side-chain blocking groups and of the peptide-resin link depends upon the differences in the rate of acidolytic cleavage. Orthoganol systems have been introduced in which the side-chain blocking groups and the peptide-resin link are completely stable to the reagent used to remove the α-protecting group at each step of the synthesis. The most common of these methods involves the 9-fluorenylmethyloxycarbonyl (Fmoc) approach. Within this method, the side-chain protecting groups and the peptide-resin link are completely stable to the secondary amines used for cleaving the N-α-Fmoc group. The side-chain protection and the peptide-resin link are cleaved by mild acidolysis. The repeated contact with base makes the Merrifield resin unsuitable for Fmoc chemistry, and β-alkoxybenzyl esters linked to the resin are generally used. Deprotection and cleavage are generally accomplished using TFA.

Those of ordinary skill in the art will recognize that, in solid phase synthesis, deprotection and coupling reactions must go to completion and the side-chain blocking groups must be stable throughout the entire synthesis. In addition, solid phase synthesis is generally most suitable when peptides are to be made on a small scale.

Acetylation of the N-terminus can be accomplished by reacting the final peptide with acetic anhydride before cleavage from the resin. C-amidation may be accomplished using an appropriate resin such as methylbenzhydrylamine resin using the Boc technology.

Following synthesis of a linear peptide, cyclization may be achieved if desired by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. This method suffers from the disadvantage of being slow but has the advantage of only producing $H_2O$ as a side product. Alternatively, strong oxidizing agents such as $I_2$ and $K_3Fe(CN)_6$ can be used to form disulfide linkages. Those of ordinary skill in the art will recognize that care must be taken not to oxidize the sensitive side chains of Met, Tyr, Trp or His. Cyclic peptides produced by this method require purification using standard techniques, but this oxidation is applicable at acid pHs. Oxidizing agents also allow concurrent deprotection/oxidation of suitable S-protected linear precursors to avoid premature, nonspecific oxidation of free cysteine.

DMSO, unlike $I_2$ and $K_3Fe(CN)_6$, is a mild oxidizing agent which does not cause oxidative side reactions of the nucleophilic amino acids mentioned above. DMSO is miscible with $H_2O$ at all concentrations, and oxidations can be performed at acidic to neutral pHs with harmless byproducts. Methyltrichlorosilane-diphenylsulfoxide may alternatively be used as an oxidizing agent, for concurrent deprotection/oxidation of S-Acm, S-Tacm or S-t-Bu of cysteine without affecting other nucleophilic amino acids. There are no polymeric products resulting from intermolecular disulfide bond formation. Suitable thiol-containing residues for use in such oxidation methods include, but are not limited to, cysteine, β,β-dimethyl cysteine (penicillamine or Pen), β,β-tetramethylene cysteine (Tmc), β,β-pentamethylene cysteine (Pmc), β-mercaptopropionic aid (Mpr), β,β-pentamethylene-β-mercaptopropionic acid (Pmp), 2-mercaptobenzene, 2-mercaptoaniline and 2-mercaptoproline.

Within another embodiment, cyclization may be achieved by amide bond formation. For example, a peptide bond may be formed between terminal functional groups (i.e., the amino and carboxy termini of a linear peptide prior to cyclization), with or without an N-terminal acetyl group and/or a C-terminal amide. Within another such embodiment, the linear peptide comprises a D-amino acid. Alternatively, cyclization may be accomplished by linking one terminus and a residue side chain or using two side chains, with or without an N-terminal acetyl group and/or a C-terminal amide. Residues capable of forming a lactam bond include lysine, ornithine (Orn), α-amino adipic acid, m-aminomethylbenzoic acid, α,β-diaminopropionic acid, glutamate or aspartate.

Methods for forming amide bonds are well known in the art and are based on well established principles of chemical reactivity. Within one such method, carbodiimide-mediated lactam formation can be accomplished by reaction of the carboxylic acid with DCC, DIC, EDAC or DCCI, resulting in the formation of an O-acylurea that can be reacted immediately with the free amino group to complete the cyclization. The formation of the inactive N-acylurea, resulting from O→N migration, can be circumvented by converting the O-acylurea to an active ester by reaction with an N-hydroxy compound such as 1-hydroxybenzotriazole, 1-hydroxysuccinimide, 1-hydroxynorbornene carboxamide or ethyl 2-hydroximino-2-cyanoacetate. In addition to minimizing O→N migration. these additives also serve as catalysts during cyclization and assist in lowering racemization. Alternatively, cyclization can be performed using the azide method, in which a reactive azide intermediate is generated from an alkyl ester via a hydrazide. Hydrazinolysis of the terminal ester necessitates the use of a t-butyl group for the protection of side chain carboxyl functions in the acylating component. This limitation can be overcome by using diphenylphosphoryl acid (DPPA), which furnishes an azide directly upon reaction with a carboxyl group. The slow reactivity of azides and the formation of isocyanates by their disproportionation restrict the usefulness of this method. The mixed anhydride method of lactam formation is widely used because of the facile removal of reaction by-products. The anhydride is formed upon reaction of the carboxylate anion with an alkyl chloroformate or pivaloyl chloride. The attack of the amino component is then guided to the carbonyl carbon of the acylating component by the electron donating effect of the alkoxy group or by the steric bulk of the pivaloyl chloride t-butyl group, which obstructs attack on the wrong carbonyl group. Mixed anhydrides with phosphoric acid derivatives have also been successfully used. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. The last few years have witnessed the development of benzotriazolyloxytris-(dimethylamino) phosphonium hexafluorophosphonate (BOP) and its congeners as advantageous coupling reagents. Their performance is generally superior to that of the well established carbodiimide amide bond formation reactions.

Within a further embodiment, a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC) and then reacted with the side chain of any of the thiol containing residues mentioned above to form a thioether linkage. In order to form dithioethers, any two thiol containing side-chains can be reacted with dibromoethane and diisopropylamine in DMF. Cyclization may also be achieved using $\delta_1,\delta_1$-Ditryptophan (i.e., Ac-Trp-Gly-Gly-Trp-OMe) (SEQ ID NO:32).

For longer peptide modulating agents, recombinant methods are preferred for synthesis. Within such methods, all or part of a modulating agent can be synthesized in living cells, using any of a variety of expression vectors known to those of ordinary skill in the art to be appropriate for the particular host cell. Suitable host cells may include bacteria, yeast cells, mammalian cells, insect cells, plant cells, algae and other animal cells (e.g., hybridoma, CHO, myeloma). The DNA sequences expressed in this manner may encode portions of an endogenous β-catenin and/or other sequences. Endogenous β-catenin sequences may be prepared based on known cDNA or genomic sequences (see Wheelock et al., *Current Topics in Membranes* 43:169–185, 1996), which may be isolated by screening an appropriate library with probes designed based on such known sequences. Screens may generally be performed as described in Sambrook et al., *Molecular Cloning. A Laboratory Manual,* Cold Spring Harbor Laboratories, Cold Spring Harbor, N.Y., 1989 (and references cited therein). Polymerase chain reaction (PCR) may also be employed, using oligonucleotide primers in methods well known in the art, to isolate nucleic acid molecules encoding all or a portion of an endogenous β-catenin. To generate a nucleic acid molecule encoding a desired modulating agent, an endogenous β-catenin sequence may be modified using well known techniques. Alternatively, portions of the desired nucleic acid sequences may be synthesized using well known techniques, and then ligated together to form a sequence encoding the modulating agent.

As noted above, a modulating agent preferably comprises an internalization moiety. An internalization moiety is any moiety (such as a compound, liposome or particle) that can be used to improve the ability of an agent to penetrate the lipid bilayer of the cellular plasma membrane, thus enabling the agent to readily enter the cytoplasm. An internalization moiety may be linked via covalent attachment or a non-covalent interaction mediated by, for example, ionic bonds, hydrogen bonds, van der waals forces and/or hydrophobic interactions, such that the internalization moiety and modulating agent remain in close proximity under physiological conditions.

Within certain embodiments, an internalization moiety is a peptide internalization sequence. An internalization sequence may be any sequence (generally a peptide sequence) that is capable of facilitating entry of the modulating agent into the cytosol of a living cell. One suitable internalization sequence is a 16 amino acid peptide derived from the third helix of the Antennapedia protein, and having the sequence RQIKIWFQNRRMKWKK (SEQ ID NO:33; see Prochiantz, Curr. Op. Neurobiol. 6:629–34, 1996) or RQIKIWPQNRRNKWKK (SEQ ID NO:34). Analogues of this sequence (i.e., sequences having at least 25% sequence identity, such that the ability to facilitate entry into the cytosol is not diminished) may also be employed. One such analogue is KKWKKWWKKWWKKWKK (SEQ ID NO:35).

Alternatively, an internalization sequence may be unrelated to the Antennapedia sequence. Any sequence that facilitates entry to the cell, via a cell surface receptor or other means, may be employed. Protein-derived helical peptide sequences that may be used as internalization sequences includes but are not limited to, KLALKLALKLA-KAALKLA (SEQ ID NO:36; see Oehlke et al., *Biochim. Biophys. Acta* 1414:127–139, 1998, and references cited therein). Other internalization sequences include the 11 amino acid TAT protein transduction domain YGRKKRRQRRR (SEQ ID NO:37; see Nagahara et al., *Nature Medicine* 4:1449–1452, 1998) and the transduction domain of HSV VP22 (see Elliot and O'Hare, *Cell* 88:223–244, 1997).

In general, the ability of a sequence to facilitate entry into the cytosol may be evaluated in any of a variety of ways. For example, a candidate internalization sequence may be covalently linked to the sequence LXXLL (SEQ ID NO:1) and contacted with cells. The ability of such a construct to modulate a β-catenin mediated response, as described herein, may then be assessed. Alternatively, the ability of a candidate internalization sequence to cross the plasma membrane may be assessed directly using any assay known in the art. Within such any assay, an internalization sequence should result in a response that is statistically greater than that observed in the absence of internalization sequence. Preferably, an internalization sequence incorporated into a modulating agent results in a response that is comparable to, or greater than, that observed for the modulating agent comprising an internalization sequence derived from TAT, a described above.

An internalization sequence may be covalently linked to the remainder of a modulating agent. Such linkage may be generated using any of a variety of means well known in the art, either directly or by way of a spacer. In general, spacers may be amino acid residues (e.g., amino hexanoic acid) or peptides, or may be other bi- or multi-functional compounds that can be covalently linked to at least two peptide sequences. Covalent linkage may be achieved via direct condensation or other well known techniques.

Other internalization moieties may be covalently or non-covalently linked to the remainder of the modulating agent. For example, the β-catenin derived portion of the modulating agent may be encapsulated by the liposome (i.e., an artificial membrane vesicle), using well known technology. Other internalization moieties include, but are not limited to, antibodies and ligands that bind to cell surface receptors. Alternatively, a polynucleotide encoding a modulating agent may be incorporated into an appropriate viral vector, such that the modulating agent is generated within the target cell. Various particle-mediated delivery systems are also available, and their use is well known to those of ordinary skill in the art.

EVALUATION OF MODULATING AGENT ACTIVITY

As noted above, modulating agents are capable of modulating β-catenin mediated gene transcription. This ability may generally be evaluated using any suitable assay known to those of ordinary skill in the art to directly evaluate β-catenin mediated gene transcription (e.g., using amplification or hybridization techniques to evaluate the level of mRNA corresponding to a gene that is transcribed in response to β-catenin). Alternatively, the effect of a modulating agent on a response associated with β-catenin mediated gene transcription may be measured. For example, differentiation may be assessed using the keratinocyte differentiation assay provided herein. Briefly, keratinocytes may be treated with a candidate modulating agent (e.g., 1 mg/ml for 48 hours). Treated and untreated cells are then photographed. At a concentration of 1 mg/ml, a modulating agent should detectably modulate the formation of terminally differentiated cells known as squams, which may be identified based on detachment from the substratum, and morphological alterations that are well known to those of ordinary skill in the art. Preferably, a modulating agent inhibits differentiation of keratinocytes.

Other suitable assays are those designed to detect changes in hair growth. Such assays may be performed using plucked hair or hair follicles cultured in vitro. Such assay are described, for example, within U.S. Pat. Nos. 5,527,772 and 5,739,111. For assays using hair, the effect of a modulating agent may be determined based on DNA content in the hair. Changes in DNA content should be observed in hair cultured for 48 hours in the presence of 1 mg/ml modulating agent, relative to hair cultured in the absence of modulating agent. In vivo assays may be performed, for example, by application of a modulating agent to shaved skin on a mouse, in which a modulating agent results in altered hair density and/or hair length. Preferred modulating agents inhibit hair growth within such assays.

MODULATING AGENT MODIFICATION AND FORMULATIONS

A modulating agent as described herein may, but need not, be linked to one or more additional molecules. Although modulating agents as described herein may preferentially bind to specific tissues or cells, and thus may be sufficient to target a desired site in vivo, it may be beneficial for certain applications to include an additional targeting agent.

Accordingly, a targeting agent may be associated with a modulating agent to facilitate targeting to one or more specific tissues. As used herein, a "targeting agent" may be any substance (such as a compound or cell) that, when associated with a modulating agent enhances the transport of the modulating agent to a target tissue, thereby increasing the local concentration of the modulating agent. Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site. Among the many monoclonal antibodies that may serve as targeting agents are anti-TAC, or other interleukin-2 receptor antibodies; 9.2.27 and NR-ML-05, reactive with the 250 kilodalton human melanoma-associated proteoglycan; and NR-LU-10, reactive with a pancarcinoma glycoprotein. An antibody targeting agent may be an intact (whole) molecule, a fragment thereof, or a functional equivalent thereof. Examples of antibody fragments are F(ab')2, -Fab', Fab and F[v] fragments, which may be produced by conventional methods or by genetic or protein engineering. Linkage is generally covalent and may be achieved by, for example, direct condensation or other reactions, or by way of bi- or multi-functional linkers. Within other embodiments, it may also be possible to target a polynucleotide encoding a modulating agent to a target tissue, thereby increasing the local concentration of modulating agent. Such targeting may be achieved using well known techniques, including retroviral and adenoviral infection.

For certain embodiments, it may be beneficial to also, or alternatively, link a drug to a modulating agent. As used herein, the term "drug" refers to any bioactive agent intended for administration to a mammal to prevent or treat a disease or other undesirable condition. Drugs include hormones, growth factors, proteins, peptides and other compounds. The use of certain specific drugs within the context of the present invention is discussed below.

Within certain aspects of the present invention, one or more modulating agents as described herein may be present within a pharmaceutical composition. A pharmaceutical composition comprises one or more modulating agents in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. One or more modulating agents (alone or in combination with a targeting agent and/or drug) may, but need not, be encapsulated within liposomes using well known technology. Compositions of the present invention may be formulated for any appropriate manner of administration, including for example, topical, oral, nasal, intravenous, intracranial, intraperitoneal, subcutaneous, or intramuscular administration.

A pharmaceutical composition may also, or alternatively, contain one or more drugs, which may be linked to a modulating agent or may be free within the composition. Virtually any drug may be administered in combination with a modulating agent as described herein, for a variety of purposes as described below. Examples of types of drugs that may be administered with a modulating agent include analgesics, anesthetics, antianginals, antifungals, antibiotics, anticancer drugs (e.g., taxol or mitomycin C), antiinflammatories (e,g, ibuprofen and indomethacin), anthelmintics, antidepressants, antidotes, antiemetics, antihistamines, antihypertensives, antimalarials, antimicrotubule agents (e.g., colchicine or vinca alkaloids), antimigraine agents, antimicrobials, antiphsychotics, antipyretics, antiseptics, anti-signaling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, narcotic antagonists, parasympathomimetics, sedatives, stimulants, sympathomimetics, toxins (e.g., cholera toxin), tranquilizers and urinary antiinfectives.

The compositions described herein may be administered as part of a sustained release formulation (i.e., a formulation such as a capsule or sponge that effects. a slow release of modulating agent following administration). Such formulations may generally be prepared using well known technology and administered by, for example, oral, rectal or subcutaneous implantation, or by implantation at the desired target site. Sustained-release formulations may contain a modulating agent dispersed in a carrier matrix and/or contained within a reservoir surrounded by a rate controlling membrane (see, e.g., European Patent Application 710,491 A). Carriers for use within such formulations are biocompatible, and may also be biodegradable; preferably the formulation provides a relatively constant level of modulating agent release. The amount of modulating agent contained within a sustained release formulation depends upon the site of implantation, the rate and expected duration of release and the nature of the condition to be treated or prevented.

Pharmaceutical compositions of the present invention may be administered in a manner appropriate to the disease to be treated (or prevented). Appropriate dosages and a suitable duration and frequency of administration will be determined by such factors as the condition of the patient, the type and severity of the patient's disease and the method of administration, In general, an appropriate dosage and treatment regimen provides the modulating agent(s) in an amount sufficient to provide therapeutic and/or prophylactic benefit. Within particularly preferred embodiments of the invention, a modulating agent or pharmaceutical composition as described herein may be administered at a dosage ranging from 0.001 to 50 mg/kg body weight, preferably from 0.1 to 20 mg/kg, on a regimen of single or multiple daily doses. For topical administration, a cream typically comprises an amount of modulating agent ranging from 0.00001% to 1%, preferably 0.0001% to 0.002%. Fluid compositions typically contain about 10 ng/ml to 5 mg/ml, preferably from about 10 $\mu$g to 2 mg/mL modulating agent. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

MODULATING AGENT METHODS OF USE

In general, the modulating agents and compositions described herein may be used for modulating $\beta$-catenin mediated gene transcription. Such modulation may be performed in vitro and/or in vivo, preferably in a mammal such as a human. Within each of the methods described herein, one or more modulating agents may generally be administered alone, or within a pharmaceutical composition. In each specific method described herein, as noted above, a targeting agent may be employed to increase the local concentration of modulating agent at the target site.

β-catenin mediated gene transcription may be modulated in any of a variety of contexts. As used herein, the phrase "β-catenin mediated gene transcription" refers to the transcription of any gene that increases in the presence of increased levels of cytosolic β-catenin. Such genes include, but are not limited to, genes that are activated by the Wnt-mediated signaling pathway, such as c-myc (see He et al., $Science$ 281:1509–12, 1998).

To modulate β-catenin mediated gene transcription in a cell, the cell may be contacted with a modulating agent as described herein. The step of contacting may be performed using any method that is suitable for the particular cell type. In vitro, for example, contacting may be achieved by adding modulating agent to the growth medium. In vivo, contact may be achieved by administration, as described herein. For administration to skin cells, topical administration is generally preferred. Contact is performed using an amount of agent and for a sufficient duration to result in a detectable change in the level of β-catenin mediated gene transcription. Such a change may be detected directly (e.g., amplification or hybridization techniques), or indirectly, based on modulation of cellular differentiation.

Contact with a modulating agent as described above further results in altered levels of activation of β-catenin mediated gene transcription in the cell. Such an affect may be readily detected using any standard method for detecting changes in transcription, such as hybridization techniques and amplification techniques involving polymerase chain reaction (PCR). Alternatively, downstream effects of such transcription may be detected. Such downstream effects may include, but are not limited to, terminal differentiation and hair growth.

As noted above, contact of a cell with a modulating agent as described herein may inhibit terminal differentiation of the cell. Accordingly, the present. invention provides methods for using a modulating agent to inhibit differentiation in a cell (e.g., a keratinocyte, stem cell, hematopoetic stem cell., germ cell or neuronal precursor cell). Cells in which differentiation may be inhibited include, but are not limited to populations of cells that are maintained in vitro. For example, stem cell populations may be maintained undifferentiated in vitro in the presence of a modulating agent. Following transplantation to a patient, and removal of the modulating agent, the cells differentiate. Such cells may be used, for example, to repopulate bone marrow following whole body irradiation. Terminal differentiation may be detected by photographic methods, based on standard criteria that are well known in the art. For example, one sign of keratinocyte terminal differentiation is the loss of intermediate filament bundles.

Contact of a skin cell with a modulating agent may further modulate (e.g., inhibit) hair growth. For such applications, administration is preferably achieved by direct contact with the skin of the mammal (e.g., by topical application or cutaneous injection). Decreased hair growth may be detected based on decreased hair density and/or rate of growth.

Modulating agents provided herein may further modulate the activity of receptors such as retinoic acid and/or androgen receptors. It has been found, within the context of the present invention, that β-catenin augments retinoic acid (vitamin A) receptor dependent transactivation. Accordingly, contact of a cell with a modulating agent may modulate the activity of such receptors in the cell.

Within further aspects, modulating agents provided herein may be used to treat cancer and/or inhibit cancer metastasis in a patient. Such agents should enhance β-catenin mediated gene transcription, resulting in enhanced cellular differentiation.

Modulating agents that enhance β-catenin mediated gene transcription may also be used to inhibit the development of Alzheimer's disease. Within such methods, a modulating agent may be administered to a patient that is at risk for developing Alzheimer's disease (but without detectable symptoms), or may be administered following diagnosis of the disease, based on clinical parameters that are accepted by those skilled in the art. Modulating agents may be administered to a patient alone or in combination with other therapeutic agents. In general, a modulating agent is administered in an amount sufficient to delay the onset, slow the progression or effect all improvement in symptoms of the disease.

The following Example is offered by way of illustration and not by way of limitation.

EXAMPLE 1

Effect of β-Catenin on Retinoic Acid Receptor Dependent Transactivation

This Example illustrates the effect of β-catenin on retinoic acid receptor activity.

Figure 1:
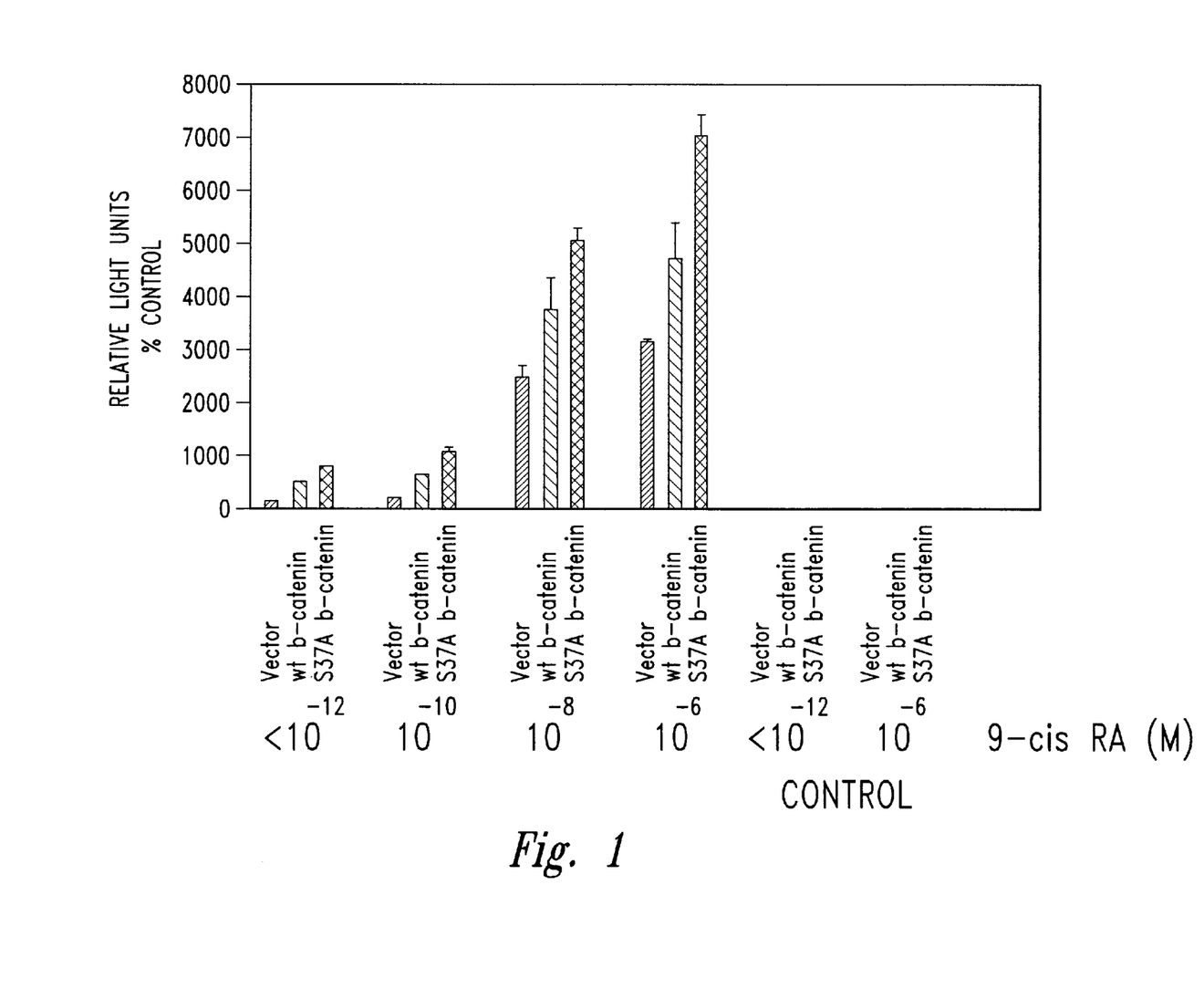
FIG. 1 is a histogram depicting the enhancement of retinoic acid receptor-dependent transactivation by β-catenin. Luciferase activity, shown in relative light units, is illustrated for MCF-7 breast cancer cells transfected with the retinoic acid β promoter-luciferase reporter plasmid and a wild-type or a stable (S37A) mutant form of β-catenin (or vector alone, as a control) and treated with the indicated doses of 9-cis retinoic acid for 48 hours. Columns indicated as control (reporter vector without the specific retinoic acid receptor sequences) showed no detectable retinoic acid receptor dependent transactivation.

MCF-7 breast cancer cells were transfected with the retinoic acid β promoter-luciferase reporter plasmid and a wild-type or a stable (S37A) mutant form of β-catenin (see Orford et al., $J. Biol. Chem.$ 272:24735–24738, 1997), and treated with various doses of 9-cis retinoic acid for 48 hours. The results, presented in FIG. 1, illustrate the activity of the reporter, measured in relative light units. At all concentrations of retinoic acid, β-catenin was found to augment the activity of the reporter. This effect was found to be more marked at the lower concentrations of retinoic acid, which indicates that β-catenin can potentiate the action of retinoic acid.

From the foregoing, it will be evident that although specific embodiments of the invention have been described herein for the purpose of illustrating the invention, various modifications may be made without deviating from the spirit and scope of the invention. Accordingly, the present invention is not limited except as by the appended claims.

What is claimed is:

1. A method for modulating β-catenin mediated gene transcription in a cell, comprising contact;ng a cell with a modulating agent that comprises an internalization moiety and one or more of:
   (a) the amino acid sequence LXXLL (SEQ ID NO:1), wherein each X is an independently selected amino acid residue, or
   (b) a peptide analogue or peptidomimetic of the amino acid sequence LXXLL (SEQ ID NO:1) which retains the ability to inhibit a β-catenin mediated response;
   and thereby modulating β-catenin mediated gene transcription in the cell.

2. A method according to claim 1, wherein the modulating agent comprises an internalization moiety and the linear peptide sequence LXXLL (SEQ ID NO:1).

3. A method according to claim 2, wherein the peptide sequence is selected from the group Consisting of IPELTKLL (SEQ ID NO:6), PELTKLLN (SEQ ID NO:7), ELTKLLND (SEQ ID NO:8) LTKLLNDE (SEQ ID NO:9), ITTLHNLL (SEQ ID NO:10), TTLHNLLL (SEQ ID NO:11), TLHNLLLH (SEQ ID NO:12), LHNLLLHQ (SEQ ID NO:13), LGTLVQLL (SEQ ID NO:14), GTLVQLLG (SEQ ID NO:15), TLVQLLGS (SEQ ID NO:16), LVQLLGSD (SEQ ID NO:17), IPRLVQLL (SEQ ID NO:18), PRLVQLLV (SEQ ID NO:19), RLVQLLVR (SEQ ID NO:20), LVQLLVRA (SEQ ID NO:21), TAPLTELL (SEQ ID NO:22), APLTELLH (SEQ ID NO:23), PLTELLHS (SEQ ID NO:24) and LTELLHSR (SEQ ID NO:25).

4. A method according to claim 1, wherein the modulating agent comprises an internalization moiety and the sequence LXXLL (SEQ ID NO:1) present within a cyclic peptide.

5. A method according to claim 1, wherein the internalization moiety is a peptide internalization sequence.

6. A method according to claim 5, wherein the internalization sequence comprises a sequence selected from the group consisting of RQIKIWFQNRRMKWKK (SEQ ID NO:33), RQIKIWPQNRRNKWKK (SEQ ID NO:34) and YGRKKRRQRRR (SEQ ID NO:37).

7. A method according to claim 1, wherein the internalization moiety is a liposome.

8. A method according to claim 1, wherein the internalization moiety is an antibody or ligand that binds to a cell surface receptor.

9. A method according to claim 1, wherein the modulating agent is linked to a targeting agent.

10. A method according to claim 1, wherein the modulating agent is linked to a drug.

11. A method according to claim 1, wherein the modulating agent is present within a pharmaceutical composition comprising a pharmaceutically acceptable carrier.

12. A method according to claim 11, wherein the composition further comprises a drug.

13. A method according to claim 11, wherein the modulating agent is present within a sustained-release formulation.

14. A method for modulating differentiation of a cell, comprising contacting a cell with a modulating agent that comprises an internalization moiety and one or more of:
   (a) the amino acid sequence LXXLL (SEQ ID NO:1) which retains the ability to inhibit a β-catenin mediated response; or
   (b) a peptide analogue or peptidomimetic of the amino acid sequence LXXLL (SEQ ID NO:1);
   and thereby modulating differentiation of the cell.

15. A method according to claim 14, wherein the modulating agent comprises an internalization moiety and the linear peptide sequence LXXLL (SEQ ID NO:1).

16. A method according to claim 15, wherein the peptide sequence is selected from the group consisting of IPELTKLL (SEQ ID NO:6), PELTKLLN (SEQ ID NO:7), ELTKLLND (SEQ ID NO:8), LTKLLNDE (SEQ ID NO:9), ITTLHNLL (SEQ ID NO:10), TTLHNLLL (SEQ ID NO:11), TLHNLLLH (SEQ ID NO:12), LHNLLLHQ (SEQ ID NO:13), LGTLVQLL (SEQ ID NO:14), GTLVQLLG (SEQ ID NO:15), TLVQLLGS (SEQ ID NO:16), LVQLLGSD (SEQ ID NO:17), IPRLVQLL (SEQ ID NO:18), PRLVQLLV (SEQ ID NO:19), RLVQLLVR (SEQ ID NO:20), LVQLLVRA (SEQ ID NO:21), TAPLTELL (SEQ ID NO:22), APLTELLH (SEQ ID NO:23), PLTELLHS (SEQ ID NO:24) and LTELLHSR (SEQ ID NO:25).

17. A method according to claim 14, wherein the modulating agent comprises an internalization moiety and the sequence LXXLL (SEQ ID NO:1) present within a cyclic peptide.

18. A method according to claim 14, wherein the internalization moiety is an internalization sequence.

19. A method according to claim 18, wherein the internalization sequence comprises a sequence selected from the group consisting of RQIKIWFQNRRMKWKK (SEQ ID NO:33), RQIKIWPQNRRNKWKK (SEQ ID NO:34) and YGRKKRRQRRR (SEQ ID NO:37).

20. A method according to claim 14, wherein the internalization moiety is a liposome.

21. A method according to claim 14, wherein the internalization moiety is an antibody or ligand that binds to a cell surface receptor.

22. A method according to claim 14, wherein the modulating agent is linked to a targeting agent.

23. A method according to claim 14, wherein the modulating agent is present within a pharmaceutical composition comprising a pharmaceutically acceptable carrier.

24. A method according to claim 14, wherein the cell is a cultured stem cell.

25. A method for modulating the activity of a retinoic acid or androgen receptor in a cell, comprising contacting a cell with a modulating agent that comprises an internalization moiety and one or more of:
   (a) the amino acid sequence LXXLL (SEQ ID NO:1);or
   (b) a peptide analogue or peptidomimetic of the amino acid sequence LXXLL (SEQ ID NO:1) which retains the ability to inhibit a β-catenin mediated response;
   and thereby modulating the activity of a retinoic acid and/or androgen receptor in the cell.

* * * * *